United States Patent [19]

Wofford

[11] Patent Number: 4,660,584
[45] Date of Patent: Apr. 28, 1987

[54] DENTAL FLOSSING DEVICE

[76] Inventor: Barry Wofford, 1102 Parkside Blvd., Toledo, Ohio 43607

[21] Appl. No.: 795,486

[22] Filed: Nov. 6, 1985

Related U.S. Application Data

[63] Continuation-in-part of Ser. No. 771,036, Aug. 30, 1985, abandoned, which is a continuation-in-part of Ser. No. 737,290, May 23, 1985, abandoned.

[51] Int. Cl.$^4$ ............................................. A61C 15/00
[52] U.S. Cl. .................................................. 132/92 A
[58] Field of Search ....................... 132/92, 93, 91, 89; 433/141

[56] References Cited

U.S. PATENT DOCUMENTS

| | | | |
|---|---|---|---|
| 677,947 | 7/1901 | Cowan | 132/92 R |
| 867,264 | 10/1907 | Evans | 132/92 R |
| 1,512,633 | 10/1924 | Peckman | 132/92 R |
| 2,577,597 | 12/1951 | Wright et al. | 132/92 R |

Primary Examiner—Robert Peshock
Attorney, Agent, or Firm—MacMillan & Sobanski

[57] ABSTRACT

An improved dental flossing device includes a generally cylindrical body portion and a curved end portion. The cylindrical body portion is hollow and includes means for mounting a spool of dental floss therein. Floss from the spool is fed through a first locking means formed within the cylindrical body to the curved end portion. The locking means consists of a cylindrical boss extending radially inwardly of the body portion which defines a through aperture. A movable member is received in the aperture therein. A passageway formed in the movable member receives the dental floss. The movable member is spring-biased such that the passageway formed therein is normally seated within the aperture formed in the boss so as to frictionally engage the dental floss and prevent movement therethrough. The floss is then threaded in a curved end portion to the tip thereof, through an aperture formed in the tip, across a gap defined between the tip of the curved end portion and the body portion, and through a second aperture formed in the end of the body portion into the interior thereof. The dental floss is lastly fed through a second locking means, similar to the first locking means and through an exit aperture formed in the body portion to the exterior thereof.

21 Claims, 20 Drawing Figures

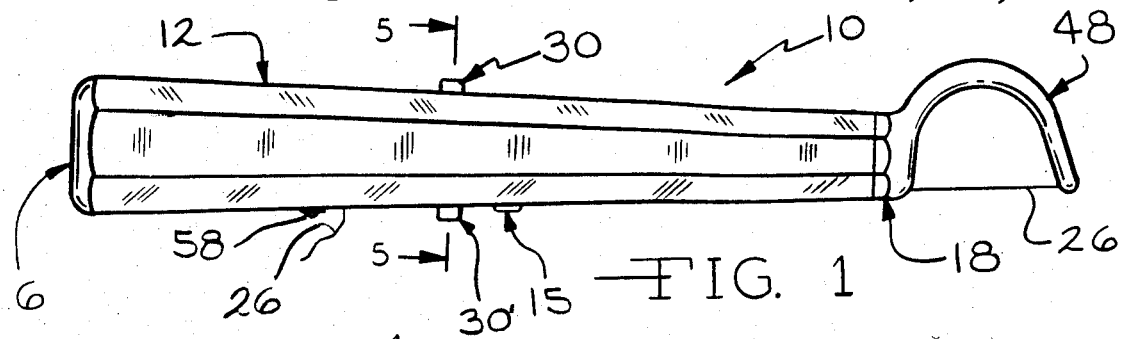
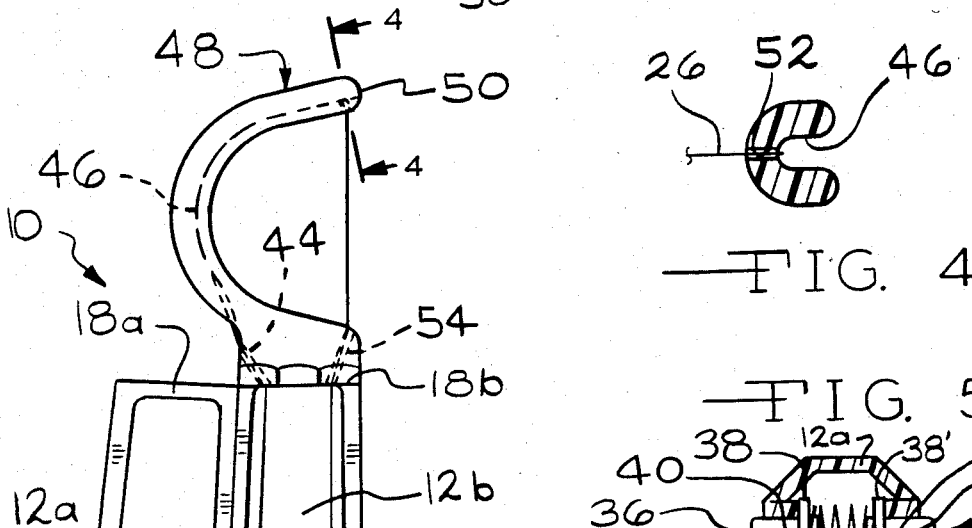
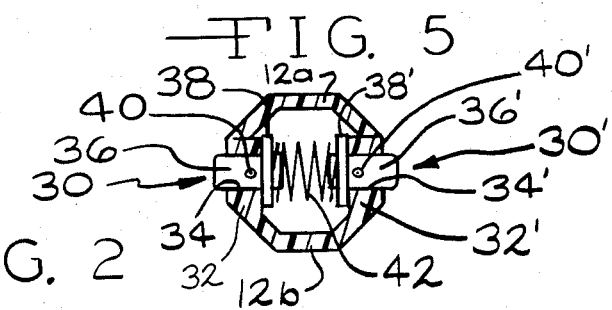
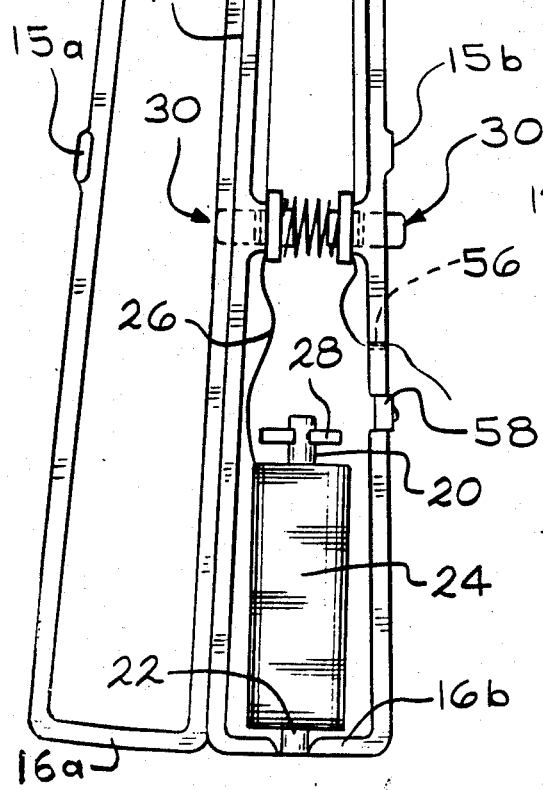
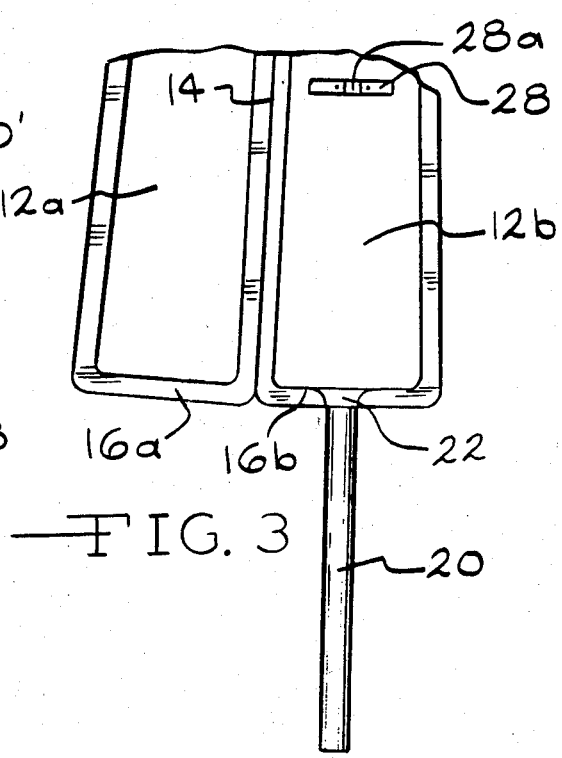

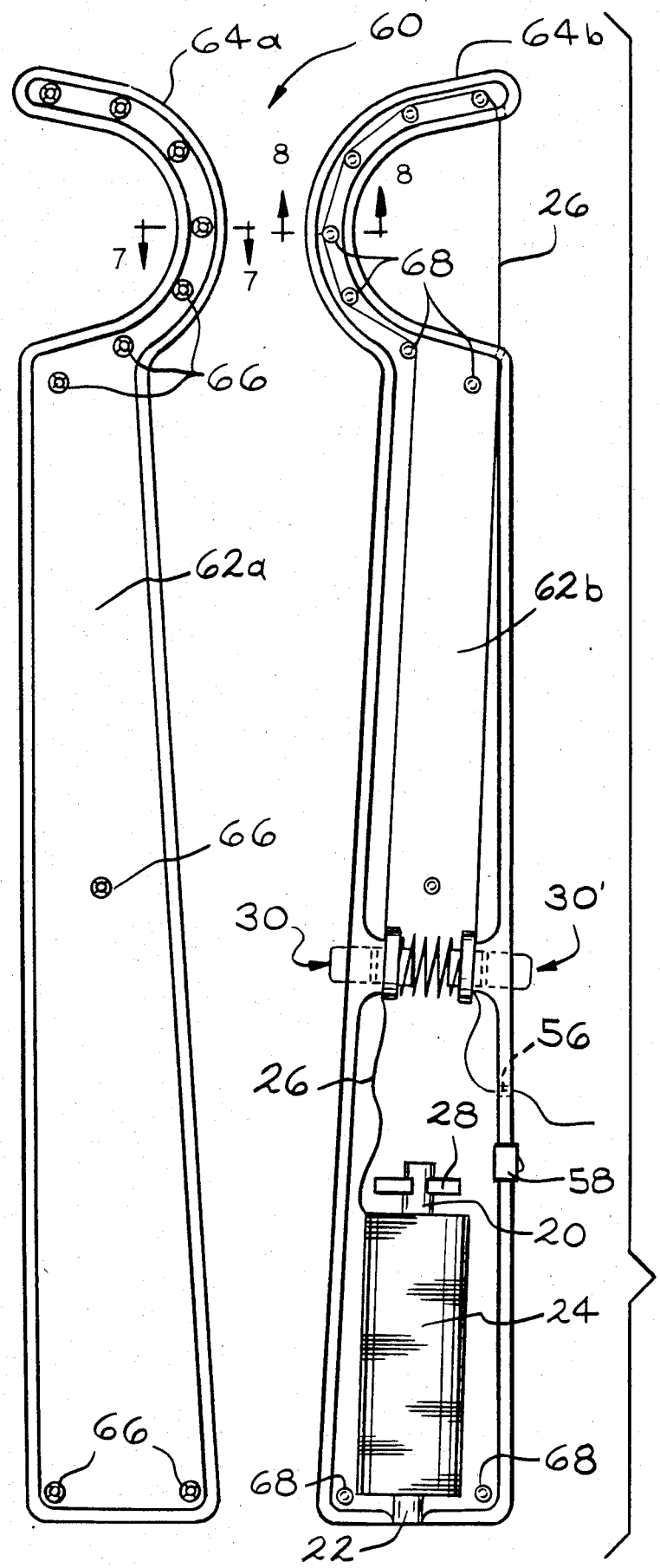
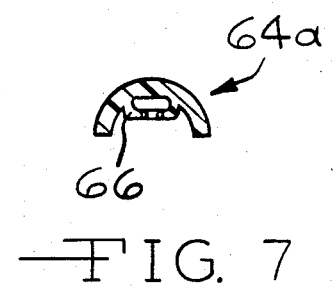
FIG. 7
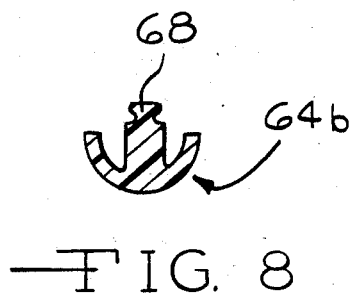
FIG. 8
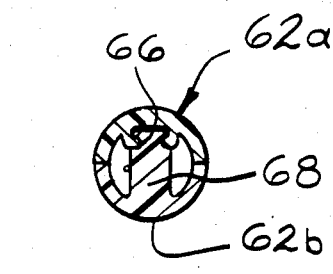
FIG. 9
FIG. 6

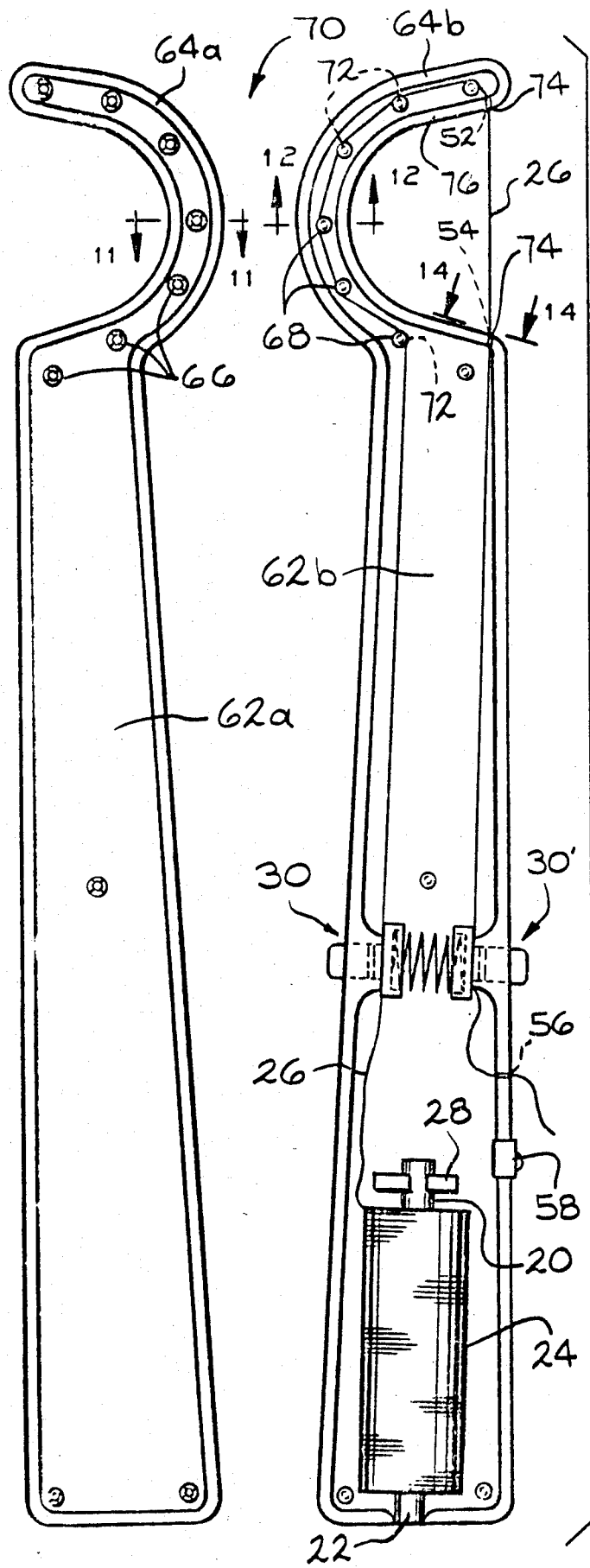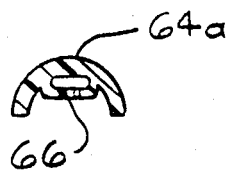
FIG. 11
FIG. 12
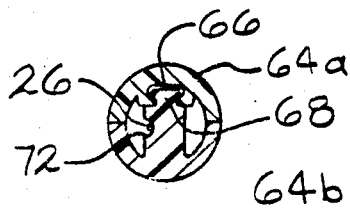
FIG. 13
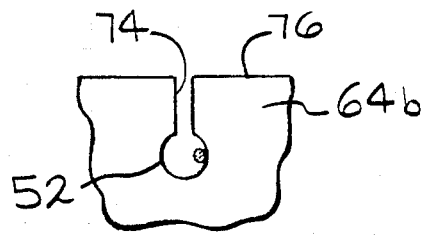
FIG. 14
FIG. 10
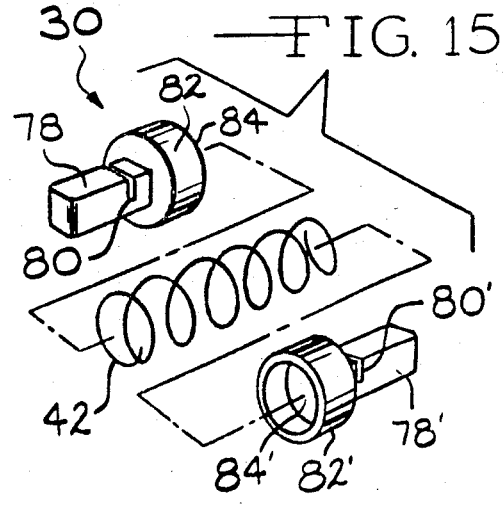
FIG. 15

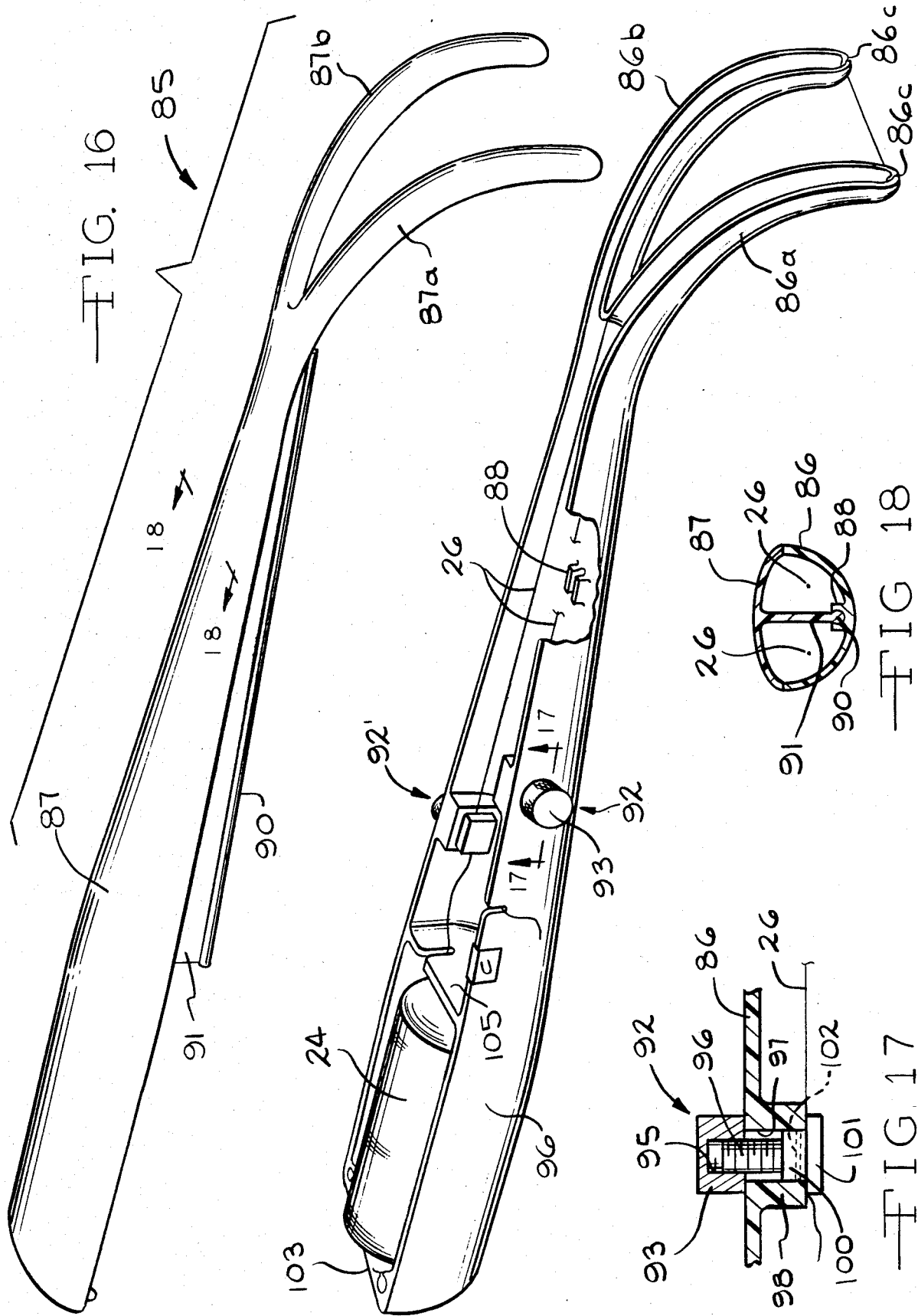

DENTAL FLOSSING DEVICE

CROSS-REFERENCE TO RELATED APPLICATION

This application is a continuation-in-part application of U.S. patent application Ser. No. 771,036, filed Aug. 30, 1985, which was a continuation-in-part application of U.S. patent application Ser. No. 737,290, filed May 23, 1985, both now abandoned.

BACKGROUND OF THE INVENTION

1. Field Of The Invention

The present invention relates in general to devices for promoting dental hygiene and in particular to an improved dental flossing device.

It is well accepted that the use of dental floss is important in maintaining good dental hygiene. Such use involves the insertion and removal of a thread of the dental floss between adjacent teeth so as to remove foreign substances lodged therein. However, the proper use of dental floss (in many cases, the total use of dental floss) is resisted by persons who dislike or who are unable to manipulate the dental floss with their fingers, especially in the innermost portions of the mouth where such flossing is particularly important.

2. Description Of The Prior Art

Many devices are known for making the use of dental floss easier. One representative device is disclosed in U.S. Pat. No. 3,915,178 to Zellers. The Zellers dental floss applicator includes a hollow cylindrical body fitted with a pair of hollow arms which are oriented to form a yoke. A rotatable spindle of dental floss is mounted in an internal chamber of the body. The thread of dental floss is fed from the spindle through a first passageway in the body to one arm, across the open section of the yoke to the other arm, and through a second passageway in the body back to the internal chamber. The thread of dental floss is lastly fed through an exterior opening in the side of the body. The openings of the two passageways in the internal chamber, leading to and from the arms, are located on a tapered section of the interior chamber. The end of the spindle facing the tapered section is formed with a mating tapered projection which can be pressed against the dental floss threads leading in and out of the passageways when a threaded end cap, mounted at the other end of the spindle, is rotated to cause such engagement. Thus, the dental floss is locked in position for use. Loosening of the end cap permits the dental floss to be drawn off the spindle, through the two arms, and out the exit hole of the device.

SUMMARY OF THE INVENTION

The present invention relates to an improved dental flossing device including a generally cylindrical body portion and a curved end portion. The cylindrical body portion is hollow and includes means for mounting a spool of dental floss therein. Floss from the spool is fed through a first locking means formed within the cylindrical body to the curved end portion. The locking means consists of a cylindrical boss extending radially inwardly of the body portion which defines a through aperture. A movable member is received in the aperture therein. A transverse passageway formed in the movable member receives the dental floss. The movable member is spring-biased such that the passageway formed therein is normally seated within the aperture formed in the boss so as to frictionally engage the dental floss and prevent movement therethrough. In a first embodiment of the invention, the floss is then threaded through an aperture formed in the end of the body portion and around a channel formed in the exterior of the curved end portion to the tip thereof. In a second embodiment of the invention, the dental floss is then threaded through the hollow interior of the curved end portion to the tip thereof. Afterwards, in both embodiments, the floss is threaded through an aperture formed in the tip of the curved end portion, across a gap defined between the tip of the curved end portion and the body portion, and through a second aperture formed in the end of the body portion into the interior thereof. The dental floss is lastly fed through a second locking means, similar to the first locking means and through an exit aperture formed in the body portion to the exterior thereof.

It is an object of the present invention to provide an improved dental flossing device which is simple and inexpensive in construction.

It is a further object of the present invention to provide an improved dental flossing device which is easy and safe to use by persons of any age.

Other objects and advantages of the present invention will become apparent to those skilled in the art from the following detailed description of the preferred embodiment, when read in light of the accompanying drawings.

BRIEF DESCRIPTION OF THE DRAWINGS

FIG. 1 is an elevational view of a first embodiment of an improved dental flossing device in accordance with the present invention, the body portion thereof being shown in a closed position.

FIG. 2 is an elevational view of the improved dental flossing device of FIG. 1, with the body portion thereof shown in an opened position.

FIG. 3 is an enlarged fragmentary elevational view of the hinged end portion of the body portion shown in FIG. 2.

FIG. 4 is a sectional view taken along line 4—4 of FIG. 2.

FIG. 5 is a sectional view taken along line 5—5 of FIG. 1.

FIG. 6 is an elevational view of two halves of a second embodiment of the improved dental flossing device in accordance with the present invention.

FIG. 7 is a sectional view taken along line 7—7 of FIG. 6.

FIG. 8 is a sectional view taken along line 8—8 of FIG. 6.

FIG. 9 is a sectional view illustrating the connecting members illustrated in FIGS. 7 and 8 mated together.

FIG. 10 is an elevational view of two halves of a third embodiment of the improved dental flossing device in accordance with the present invention.

FIG. 11 is a sectional view taken along line 11—11 of FIG. 10.

FIG. 12 is a sectional view taken along line 12—12 of FIG. 10.

FIG. 13 is a sectional view illustrating the connecting members illustrated in FIGS. 11 and 12 mated together.

FIG. 14 is a sectional view taken along line 14—14 of FIG. 10.

FIG. 15 is an exploded perspective view of the floss locking means of FIG. 10.

FIG. 16 is an exploded perspective view of two halves of a fourth embodiment of the improved dental flossing device in accordance with the present invention.

FIG. 17 is a sectional elevational view taken along line 17—17 of FIG. 16.

FIG. 18 is a sectional elevational view taken along line 18—18 of FIG. 16 when the halves are joined together.

DETAILED DESCRIPTION OF THE PREFERRED EMBODIMENTS

Figures 19, 20:
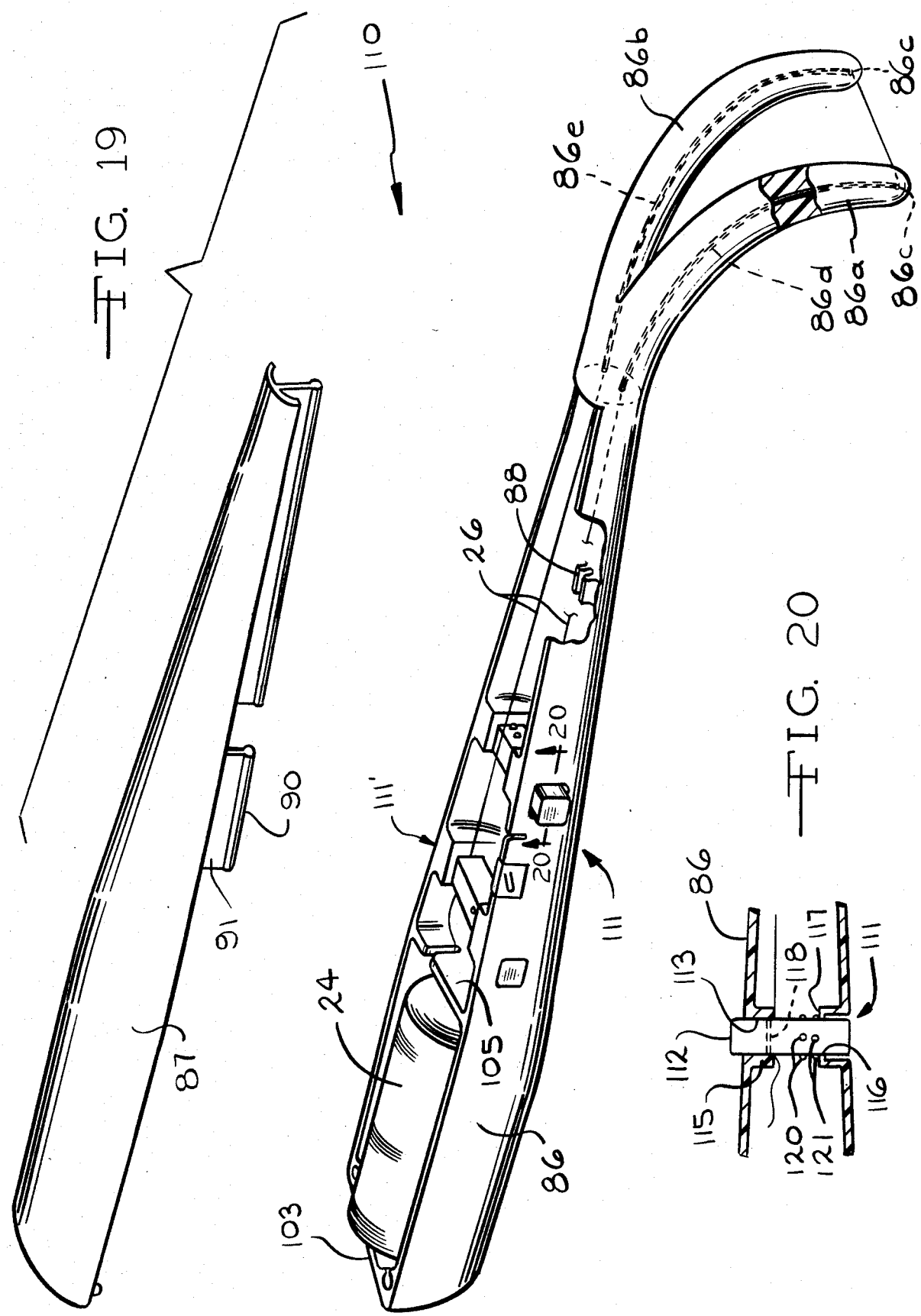
FIG. 19 is an exploded perspective view of two halves of a fifth embodiment of the improved dental flossing device in accordance with the present invention.
FIG. 20 is a sectional elevational view taken along line 20—20 of FIG. 19.

Referring now to the drawings, there is illustrated in FIGS. 1 through 5 a first embodiment of an improved dental flossing device 10 in accordance with the present invention. The dental flossing device 10 includes a body portion 12 consisting of a pair of opposed body halves 12a and 12b. The body portion 12 can be formed of any material, but preferably a relatively thick plastic material is utilized so as to make the body portion 12 somewhat rigid. As shown in FIG. 2, the body halves 12a and 12b are joined along respective sides thereof by a first hinge portion 14. The first hinge portion 14 can consist of a relatively thin web of the plastic material forming the body portion 12, so as to be flexible to permit the body halves 12a and 12b to be folded over upon one another, as illustrated in FIGS. 1 and 5, yet also to be strong to resist breakage from fatigue due to repeated opening and closings thereof. Thus, the body portion 12 and the first hinge portion 14 can be formed from the same piece of plastic material, the relative rigidity of the body portion 12 with respect to the first hinge portion 14 resulting from being formed thicker than the first hinge portion 14. A closing means 15, consisting of respective snap portions 15a and 15b, can be formed on the body halves 12a and 12b, respectively, to maintain the body halves 12a and 12b in the closed position, illustrated in FIG. 1, when desired.

The body portion 12 is generally formed in the shape of a hollow cylinder extending from a first end 16 toward a second end 18. If desired, the first end 16 can be slightly larger in diameter than the second end 18, such that the body portion 12 includes a slight taper. As with the body portion 12, the first end 16 and the second end 18 are formed by opposing end halves 16a and 16b and 18a and 18b, respectively, each being formed integral with the respective body halves 12a and 12b. The end half 16b is attached to one end of a mounting rod 20 by a second hinge portion 22. The second hinge portion 22 can be formed in the same manner as the first hinge portion 14. The mounting rod 20 is a cylindrical projection provided such that a spool 24 of a continuously wound thread of dental floss 26 can be inserted thereabout. A bracket 28 can be formed integral with the body half 12b extending inwardly. The bracket 28 is formed integral with the body half 12b and includes a recessed portion 28a for receiving and maintaining the other end of the mounting rod 20 therein when the mounting rod 20 is moved from an opened position (illustrated in FIG. 3) to a closed position (illustrated in FIG. 1). In order to load the flossing device 10 with dental floss 26, the mounting rod 20 is moved to its opened position, the spool 24 is inserted onto the mounting rod 20, and the mounting rod 20 is moved to its closed position.

The dental floss 26 is initially threaded from the spool 24 through a first locking means, indicated generally at 30. The first locking means 30 includes a generally cylindrical, inwardly-extending boss 32 formed on one side of the body half 12b. An aperture 34 is provided through the boss 32 and the body half 12. A locking pin 36 is provided in the aperture 34. The locking pin 36 has an outside diameter which is approximately equal to the inside diameter of the aperture 34. The locking pin 36 is adapted to slidably move axially within the aperture 34. A collar 38 can be provided on the locking pin 36 to limit the axial movement of the pin 36 outwardly from the interior of the body portion 12. A transverse aperture 40 is provided through the locking pin 36 to permit the dental floss 26 to be threaded therethrough. A second locking means, indicated generally at 30', is formed on the other side of the body half 12b. The second locking means 30' is identical in structure and operation to the first locking means 30, and like reference numerals are utilized to designate corresponding parts thereof. A helical compression spring 42 is provided between the locking pins 36 and 36' so as to normally urge them outwardly into locked positions, wherein the collars 38 and 38' are spaced bosses 32 and 32' and the blocking pin apertures 40 and 40' are recessed within the boss apertures 34 and 34'. The urging of the spring 42 can be overcome, such as by squeezing the two locking pins 36 and 36' together between an operator's thumb and index finger, so as to move the locking pins 36 and 36' inwardly to unlocked positions, wherein the collars 38 and 38' are spaced apart from the bosses 32 and 32' and the locking pin apertures 40 and 40' are extended into the body portion 12.

Dental floss 26 from the spool 24 is initially threaded through the aperture 40 formed in the locking pin 36 of the first locking means 30. Such threading is accomplished by manually pushing the locking pin 36 inwardly against the urging of the spring 42 as described above. In this opened position, the locking pin aperture 40 is extended out of the boss aperture 34 into the interior of the body portion 12. The locking pin 36 must be maintained in this position continuously while the dental floss 26 is threaded throughout the rest of the flossing device 10.

The dental floss 26 is next threaded through the interior of the body portion 12 to a first aperture 44 formed in the second end half 18b. The first aperture 44 communicates between the interior of the body portion 12 and a U-shaped channel 46 formed in the exterior of a curved end portion 48 of the dental flossing device 10. The dental floss 26 is carried in the channel 46 throughout the curved end portion 48 to a tip 50 thereof, wherein the dental floss 26 passes through a tip aperture 52, across a gap defined between the tip 48 of the curved end portion 46 and the second end half 18b, through a second aperture 54 formed in the second end half 18b and back into the interior of the body portion 12. The dental floss 26 is lastly threaded through the aperture 40' of the second locking means 30' (which, as with the first locking means 30, must first be moved to its opened position) and out of the interior of the body portion 12 through an exit aperture 56.

Once the dental floss 26 has been so threaded, the flossing device 10 can be operated in the following manner. The body portion 12 is adapted to be gripped by an operator as a handle to position the curved end 48 thereof in the operator's mouth. The exposed dental floss 26 in the gap of the curved end portion 48 can be easily inserted and removed between adjacent teeth by the operator, even in the innermost portions of the mouth. When being used in this manner, the locking means 30 and 30' are not engaged by the operator. As a result of the biasing action of the spring 42, the locking means 30 and 30' are maintained in their normally locked positions. In these locked positions, the thread of dental floss 26 is frictionally engaged between the locking pins 30 and 30' and the respective bosses 32 and 32', thus preventing longitudinal movement of the thread 26 therein. Being tightly engaged in this manner at both ends, the exposed portion of the dental floss 26 in the gap of the closed end portion 48 is maintained taut for use during flossing.

When the exposed portion of the dental floss 26 becomes worn, the present invention provides a simple method of advancing the dental floss 26 such that a new portion thereof is exposed for use. The operator merely squeezes the exposed portions of the locking pins 36 and 36' together so as to move them inwardly toward one another to their unlocked positions. As mentioned above, the locking pin apertures 40 and 40' are extended out of their respective boss apertures 34 and 34' to permit the dental floss 26 to move freely therethrough. The end of the dental floss 26 extending out of an exit aperture 56 can then be pulled so as to advance the dental floss 26 from the spool 24 and throughout the flossing device 10 until an unused portion of the dental floss 26 is exposed in the gap of the closed end portion 48. If desired, a cutting edge 58 can be formed integral with the exterior of the body half 12b to provide a means for trimming the length of the dental floss 26 extending out the exit aperture 56.

FIGS. 6 through 9 illustrate a second embodiment of an improved dental flossing device 60 in accordance with the present invention. To the extent that the second flossing device 60 is identical to the first flossing device 10, like reference numerals will be utilized therein. The second flossing device 60 is basically identical to the first flossing device except that respective body halves 62a and 62b are not joined together by a hinge portion. Rather, each of the body halves 62a and 62b is formed as a separate member, and includes a respective curved end portion halves 64a and 64b. A plurality of female connecting members 66 are formed integral with the body half 62a and curved end portion half 64a, while a corresponding plurality of stanchion-like male connecting members 68 are formed integral with the body half 62b and curved end portion half 64b. The connecting members 66 and 68 are adapted to cooperate as illustrated in FIG. 9 to lock the respective body halves 62a and 62b and curved end portions halves 64a and 64b together for normal use of the flossing device 60. The operation of the flossing device 60 is substantially the same as described above, except that the thread of dental floss 26 can be threaded within the curved end portions halves 64a and 64b as illustrated in FIG. 6. Thus, the flossing device 60 does not include any structure corresponding to the U-shaped channel 46 of the first flossing device 10.

FIGS. 10 through 15 illustrate a third embodiment of an improved dental flossing device 70 in accordance with the present invention. To the extent that the third flossing device 70 is identical to the first and second flossing devices 10 and 60, respectively, like reference numerals have been utilized therein. The third flossing device 70 includes the mounting rod 20, the hinge portion 22, the spool of dental floss 24, the thread of dental floss 26, the brackets 28, the locking means 30, the exit aperture 56, the cutting edge 58, the body halves 62a and 62b, the female connecting members 66, and the male connecting members 68. The third flossing device 70 further includes semi-circular indentations or grooves 72 formed into the sidewalls of the male connecting members 68. The placement and orientation of the grooves 72 is such as to receive the thread 26 substantially axially therein. The grooves 72 guide the thread 26 and also assist initial threading of the curved end portion halves 64b. With reference now particularly to FIGS. 10 and 14, it will be appreciated that, in addition to the apertures 54 through which the thread 26 passes in the curved end portion halves 64b, a slot 74 is disposed. The slot 74 extends between the tip aperture 52 and the planar interior face 76 of the body half 62b. The second aperture 54 likewise includes the slot 74. The slot 74 facilitates the disposition of the dental floss 26 within the flossing device 70. The locking means of the third embodiment of the flossing device 70 includes a pair of locking pins 78 and 78'. The locking pins each define a transversely disposed slot or passageway 80 and 80', respectively, which receive the thread of dental floss 26. The passageways 80 and 80' likewise facilitate threading of the device 70 with the dental floss 26. The locking pins 80 and 80' also include a circular, axially extending wall 82 and 82' which define concentrically disposed circular recesses 84 and 84', respectively. The recesses 84 and 84' receive a helical compression spring 42 which biases the locking pins 78 and 78' away from one another and into positions illustrated in FIG. 10. Operation of the third embodiment of an improved dental flossing device 70 is the same as the operation of the first and second embodiments previously disclosed. However, the threading or installation of the dental floss 26 in the device 70 is facilitated by the incorporation of the guide grooves 72, slot 74, and passageways 80 and 80', as described immediately above.

FIGS. 16 through 18 illustrate a fourth embodiment of an improved dental flossing device 85 in accordance with the present invention. The dental flossing device 85 includes a main body 86 and a cover 87. The body 86 is provided with one or more sets of clips 88 which can be formed integrally therewith. The clips 88 are adapted to receive an enlarged end portion 90 of a longitudinally-extending flange 91 formed integrally with the cover 87. The enlarged end portion 90 is adapted to be received in each set of clips 88 so as to selectively attach the cover 87 to the main body 86. The main body 86 is provided with integral end members 86a and 86b which define a generally V-shaped forked end. If desired, the end members 86a and 86b can be curved slightly away from the longitudinal axis of the body 86 to make the dental flossing device 85 easier to utilize. The cover 87 is provided with corresponding end members 87a and 87b to close the respective end members 86a and 86b. Each of the end members 86a and 86b includes a small slit or aperture 86c for purposes described below.

Locking means, indicated generally at 92 and 92' are provided on the opposed side portions of the body 86. As shown most clearly in FIG. 17, the locking means 92 includes a rotatable knurled nut 93 having a threaded inner cavity 95. The knurled nut 93 is disposed outside of the body 86 and is adapted to grasped and rotated by a user of the dental flossing device 85. A threaded pin 96 is received in the threaded cavity 95 and extends inwardly through a square-shaped passageway 97 formed in an inwardly-extending boss 98. The boss 98 can be formed integrally with the body 86. A first head portion 100 is formed integrally with the threaded pin 96. The first head portion 100 is sized to conform generally in shape to the passageway 97. Thus, the pin 96 and the first head portion 100 are prevented from rotating relative to the body 86. However, the pin 96 and the first head portion 100 can move inwardly and outwardly through the passageway 97. A second head portion 101 can be formed integrally with the first head portion 100. The second head portion 101 is larger in size than the passageway 97 to limit the amount of movement of the pin 96 and the first head portion 100 by engaging the inner surface of the boss 98.

An aperture 102 is formed through the first head portion 100 in a direction generally parallel to the longitudinal axis of the body 86. The aperture 102 is adapted to receive the thread 26 of dental floss from the spool 24 therethrough. When the knurled nut 93 is rotated in one direction, the first head portion 100 is drawn within the aperture 97 formed by the boss 98 so as to frictionally engage the thread 26 of dental floss between the first head portion 100 and the boss 98. If the knurled nut 93 is continued to be rotated in the same direction, the second head portion 101 will eventually engage the boss 98 and frictionally grip the thread 26 of dental floss therebetween. In these situations, the thread 26 of dental floss is tightly gripped, and longitudinally movement thereof is effectively prevented. Conversely, when the knurled nut 93 is rotated in the opposite direction, the aperture 102 is moved inwardly out of the passageway 97 to permit the thread 26 of dental floss to be pulled therethrough.

To use the dental flossing device 85, the spool 24 is initially loaded within the body 86 as described above. Alternatively, the spool 24 can simply be placed within an interior cavity of the dental flossing device 85 defined by the cover 86, an end wall 103 of the body 86, an interior wall 105 formed between the side walls of the body 86, and the cover 87. The thread 26 of dental floss is then fed through the locking means 92' (the structure and operation of which are identical to the locking means 92), through the end member 86b, out the one slit 86c thereof and in the slit 86c of the other end member 86a, and back through the locking means 92. It will be appreciated that the locking means 92 and 92' permit the exposed portion of dental floss 26 between the end portions 86a and 86b to be securely gripped during use, yet permit the thread 26 to be advanced when worn.

FIGS. 19 and 20 illustrated a fifth embodiment of an improved dental flossing device 110 in accordance with the present invention. To the extent that the fifth dental flossing device 110 is identical or similar to the fourth flossing device 85, like reference numerals have been utilized therein. The end members 86a and 86b are closed and include respective passageways 86d and 86e formed therethrough for the passage of the thread 26 of dental floss. The dental flossing device 110 includes a pair of locking means 111 and 111' for gripping the thread 26 of dental floss. As shown most clearly in FIG. 20, the locking means 110 includes a square-shaped locking pin 112 oriented transversely with respect to the longitudinal axis of the body 86. One end of the locking pin 112 is received in a square-shaped aperture 113 formed in an inwardly-extending boss 115 on the body 86. The other end of the locking pin 112 is received in a square-shaped aperture 116 formed in a recessed sidewall 117 of the body 86. An aperture 118 is formed through the locking pin 112 on the end thereof retained in the boss 115. The aperture 118 is adapted to receive the thread 26 of dental floss therein for selective frictional engagement as described above.

First and second sets of circumferentially-disposed protuberances 120 and 121, respectively, are formed on the locking pin 112 near the other end thereof retained in the recessed sidewall 117. The sets of protuberances 120 and 121 are provided to retain the locking pin 112 in a desired position relative to the body 86. The ends of the locking pin 112 can be pushed by a user of the dental flossing device 110 so as to alternately engage or release the thread 26 of dental floss. The sets of protuberances 120 and 121 resist being moved through the aperture 116 because they each define an enlarged perimeter portion about the locking pin 112 which is slightly larger than the perimeter of the aperture 116. However, the sets of protuberances 120 and 121 can be forced through the aperture 116 by the application of a sufficient amount of force, since the recessed wall 117 is formed of the same resilient plastic material as the body 86. As shown in FIG. 20, the second set of protuberances 121 resists movement of the locking pin 112 in a direction which would move the aperture 118 out of the boss 115, thereby releasing the thread 26 of dental floss. By moving the locking pin 112 so that the aperture 116 is disposed between the first and second sets of protuberances 120 and 121, the locking pin 112 can be located in a position to release the thread 26 of dental floss, yet prevent the locking pin 112 from being completely withdrawn from the body 86. The operation of the dental flossing device 110 is substantially the same as described above in connection with the fourth embodiment 85.

In accordance with the provisions of the patent statutes, the principal and mode of operation of the invention has been explained and illustrated in their preferred embodiments. However, it must be understood that the present invention can be practiced otherwise than as specifically explained and illustrated without departing from its spirit or scope.

What is claimed is:

1. A dental flossing device comprising:
a hollow body portion having an interior and further having a first aperture and a second aperture formed in the hollow body portion and being adapted to receive a spool of dental floss thread in the interior of said hollow body portion thereof;
an end portion disposed at one end of said body portion and extending to a tip, said end portion including a gap exposing a thread of dental floss from said spool thereaccross;
aperture means formed between said body portion interior and said end portion for receiving said thread of dental floss therethrough; and
locking means disposed within said body portion for selectively frictionally engaging said thread of said dental floss of a pair of spaced apart locations, said locking means including a first locking pin disposed in said first aperture formed in said body portion and having a first transverse passageway formed therethrough adapted to receive said thread of dental floss, said first locking pin being movable between a first position, wherein said first transverse passageway is recessed within said first aperture such that said thread of dental floss is frictionally engaged between said first locking pin and said body portion, and a secod position of said first locking pin, wherein said first transverse passageway is extended out of said first aperture and into said interior of said body portion so as to release said thread of dental floss, said locking means further including a second locking pin disposed in second aperture formed in said body portion and having a second transverse passageway formed therethrough adapted to receive said thread of dental floss, said second locking pin being moveable independently of said first locking pin between a first position of said second locking pin, wherein said second transverse passageway is recessed within said second aperture such that said thread of dental floss is frictionally engaged between said second locking pin and said body portion, and a second position of said second locking pin, wherein said second transverse passageway is extended out of said second aperture and into said body portion interior so as to release said thread of dental floss.

2. The invention defined in claim 1 wherein said hollow body portion includes two body halves connected by a hinge portion, said body halves being movable relative to one another between an open position and a closed position.

3. The invention defined in claim 2 further including closing means for selectively maintaining said body halves in said closed position.

4. The invention defined in claim 1 wherein said hollow body portion includes two separate body halves and said end portion includes two separate end portion halves.

5. The invention defined in claim 4 further including fastening means for releasably connecting said body halves and said end portion halves together to form said hollow body portion.

6. The invention defined in claim 5 wherein said fastening means comprises a plurality of stanchions, at least one of said stanchions having a groove means for receiving said thread of dental floss.

7. The invention defined in claim 1 wherein said end portion is curved from said aperture means to said tip so as to define said gap therebetween, said curved end portion including an aperture formed therethrough for carrying said thread of dental floss.

8. The invention defined in claim 1 wherein said end portion is curved from said aperture means to said tip so as to define said gap therebetween, said curved end portion including a U-shaped channel formed in the exterior thereof for carrying said thread of dental floss.

9. The invention defined in claim 1 further including biasing means for normally urging said first locking pin toward said first position of said first locking pin and for normally urging said second locking pin toward said first position of said second locking pin.

10. The invention defined in claim 1 wherein said biasing means includes a spring.

11. The invention defined in claim 1 wherein one of said first transverse passageway and said second transverse passageway is an aperture.

12. The invention defined in claim 1 wherein one of said first transverse passageway and said second transverse passageway is a slot.

13. The invention defined in claim 1 wherein said end portion is formed with two end members in a generally V-shaped configuration so as to define said gap therebetween, said end members including respective passageways formed therethrough for carrying said thread of dental floss.

14. The invention defined in claim 1 wherein one of said first locking pin and said second locking pin includes a threaded portion and a first head portion, said threaded portion and a first head portion, said threaded portion extending outwardly from said hollow body portion and further comprising a rotatable knurled nut in threaded engagement with said threaded portion such that rotation of said knurled nut moves said threaded portion and said first head portion throughout one of said first aperture and said second aperture formed in said body portion.

15. The invention defined in claim 14 wherein said one of said first locking pin and said second locking pin includes means for preventing rotation of said one of said first locking pin and said second locking pin relative to said body portion.

16. The invention defined in claim 14 wherein one of said first aperture and said second aperture formed in said body portion and said first head portion are formed generally square in shape that rotation of said locking pin relating to said body portion is prevented.

17. The invention defined in claim 14 wherein one of said first transverse passageway and said second transverse passageway is formed through said first head portion.

18. The invention defined in claim 14 wherein one of said first locking pin and said second locking pin further includes a second head portion larger in size than one of said first aperture and said second aperture formed in said body portion so as to limit the amount of movement of said one of said first locking pin and said second locking pin therethrough.

19. A dental flossing device comprising:
a hollow body portion adapted to receive a spool of dental floss thread in the interior thereof;
and end portion disposed at one end of said body portion and extending to a tip, said end portion including a gap exposing a thread of dental floss from said spool thereaccross;
aperture means formed between said body portion interior and said end portion for receiving said thread of dental floss therethrough; and
locking means disposed within said body portion for selectively frictionally engaging said thread of said dental floss at a pair of spaced apart locations, said locking means including a locking pin and first and second spaced apart opposed apertures formed in said body portion, said locking pin being disposed in each of said first and second apertures and extending therebetween, at least one of said first and second apertures being sized to fit closely about said locking pin, said locking pin having a transverse passageway formed therethrough adapted to receive said thread of dental floss, said locking pin being moveable between a first position, wherein said transverse passageway is recessed within one of said first and second apertures such that said thread of dental floss is frictionally engaged between said locking pin and said body portion, and a second position, wherein said transverse passageway is extended out of said interior of said body portion so as to release said thread of dental floss.

20. The invention defined in claim 19 further including a first set of protuberances formed on said locking pin, said first set of protuberances defining an enlarged perimeter portion about said locking pin which is slightly larger than the perimeter of said one of said first and second apertures so as to resist movement of said locking pin therethrough out of said first position.

21. The invention defined in claim 20 further including a second set of protuberances formed about said locking pin, said second set of protuberances defining an enlarged perimeter portion about said locking pin which is slightly larger than the perimeter of said one of said first and second apertures so as to resist movement of said locking pin therethrough out of said second position.

* * * * *